(12) United States Patent
Alam (10) Patent No.: US 6,174,729 B1
(45) Date of Patent: *Jan. 16, 2001

(54) METHOD, AND KIT FOR TOTAL PROTEIN ASSAY

(76) Inventor: Aftab Alam, 9 Foxcliff Ct., St. Louis, MO (US) 63011

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/564,709

(22) Filed: Nov. 29, 1995

Related U.S. Application Data

(63) Continuation-in-part of application No. 08/370,685, filed on Jan. 10, 1995, now abandoned.

(51) Int. Cl.[7] ................................. G01N 33/49
(52) U.S. Cl. .................. 436/86; 436/63; 436/169; 422/61
(58) Field of Search ................... 422/55–58, 61; 435/4, 7.1–7.21, 805, 810, 970, 975; 436/63, 56, 169

(56) References Cited

U.S. PATENT DOCUMENTS 4,193,981 * 3/1980 Bjorkhend ........................ 424/12
5,147,780 * 9/1992 Pouletty et al. .................. 435/7.1

OTHER PUBLICATIONS

Cabib et al., "Protein Assay for Dilute Solutions", Methods Enenzymology, vol. 104 pp. 415–417.*
Kimar et al., "Fast and Efficient Method for Detection and Estimation of Proteins" Biochem, Biophys. Res Commun. (1985), 131(2), 883–91.*
Otto Folin, et al; "On Phosphotungstic–Phosphomolybdic Compounds as Color Reagents"; Jun. 29, 1912; The Journal of Biological Chemistry, vol. 12; pp. 239–243.
David Greenberg; "The Colorimetric Determination of the Serum Proteins"; Mar. 11, 1929; The Journal of Biological Chemistry, vol. 82; pp. 445–450.
Otto Folin, et al; "On Tyrosine and Tryptophane Determinations in Proteins"; Apr. 1, 1927; The Journal of Biological Chemistry, vol. 73, pp. 627–650.
Oliver Lowry, et al; "Protein Measurement with the Folin Phenol Reagent"; May 28, 1951; The Journal of Biological Chemistry, vol. 193, pp. 265–275.
Gary Peterson; "Review of the Folin Phenol Protein Quantitation Method of Lowry, Rosebrough, Farr and Randall"; The Journal of Biological Chemistry, vol. 100, pp. 201–220, No Date.
Marion Bradford; "A Rapid and Sensitive Method for the Quantitation of Microgram Quantities of Protein Utilizing the Principle of Protein–Dye Binding"; Jan. 29, 1976; Analytical Biochemistry, vol. 72, pp. 248–254.
P. Smith, et al; "Measurement of Protein Using Bicinchoninic Acid"; Apr. 30, 1985; Analytical Biochemistry, vol. 150, pp. 76–85.

(List continued on next page.)

Primary Examiner—Lyle A. Alexander (57) ABSTRACT

A method, device and kit for determining total protein concentration in a protein solution, which comprises applying the protein solution to a protein-support, wherein the protein-support is capable of retaining the total protein in the form of a protein spot having a size that is proportional to the protein concentration when the protein contacts the protein-support in the presence of a detergent and at least one of a salt or an acidic agent; measuring the size of the protein spot produced on the protein-support; and comparing the size of the protein spot with a standard.

33 Claims, 3 Drawing Sheets

OTHER PUBLICATIONS

Christa Stoscheck; "Quantitation of Protein"; 1990; Methods in Enzymology, vol. 182, pp. 50–68.

Gary Peterson; "Determination of Total Protein"; 1983; Methods in Enzymology, vol. 91, pp. 95–119.

Harumi Kuno, et al; "Simple Microassay of Protein with Membrane Filter"; Aug. 26, 1967; Nature, vol. 215, pp. 974–975.

S. Bramhall, et al; "A Simple Colorimetric Method for Determination of Protein"; Apr. 2, 1969; Analytical Biochemistry, vol. 31, pp.146–148.

L. Minamide, et al; "A Filter Paper Dye–Binding Assay for Quantitative Determination of Protein without Interference from Reducing Agents or Detergents"; May 17, 1990; Analytical Biochemistry, vol. 190, pp. 66–70.

B. Vijaya Kumar, et al; "Fast and Efficient Method for Detection and Estimation of Proteins"; May 16, 1985; Biochemical and Biophysical Research Communications, vol. 131, pp. 883–891.

* cited by examiner

METHOD, AND KIT FOR TOTAL PROTEIN ASSAY

CROSS-REFERENCE TO RELATED APPLICATIONS

This application is a continuation-in-part of Applicant's U.S. patent application Ser. No. 08/370,685, filed Jan. 10, 1995 now abandoned which is incorporated herein in its entirety by reference.

BACKGROUND OF THE INVENTION

1. Field of the Invention

This invention relates to a method, device and kit for estimation of total protein in a sample.

2. Description of the Related Art

Proteins are the essential components of life processes and thus play a central role in biological research as well as many commercial processes. The study and use of proteins inevitably requires quantifying the amount of protein in a sample.

Over the last hundred years several methods have been developed for estimation of total protein concentration, also referred to herein as protein assay. The biuret, refractometric and total nitrogen methods are amongst the earliest examples of protein estimation. The biuret method relies on the reaction of alkaline copper with the peptide bonds of protein which gives a characteristic purple color; unfortunately this method is not very sensitive for total protein estimation and thus it is not widely used.

At the turn of this century, Folin and Denis (J. Biol. Chem., 12:239–243 (1912), incorporated herein by reference) developed a phospho-molybdictungstic acid, commonly known as Folin reagent, which shows a strong color reaction with many phenol derivatives, including tyrosine and tryptophan. The development of the Folin reagent began an intense era in the development of colori-inetric protein assays using the Folin reagent, as demonstrated by the publication of such methods by a number of researchers, including Greenberg (J. Biol. Chem., 82:545 (1929), and Folin and Ciocalteu (J. Biol. Chem., 73:627 (1927)), each of which is incorporated herein by reference. Then, in 1951, Lowry et al (J. Biol. Chem. 193:265–275, incorporated herein by reference) published their classical and comprehensive work for protein estimation using the Folin reagent, known as the Lowry method. From 1951 until the present, the Lowry method, including various modifications thereof, remained unrivaled and is currently regarded as the standard method for protein estimation.

Despite the wide application of the Lowry method over the last fifty years, the Lowry method suffers from numerous and well recognized drawbacks. In a nutshell, the Lowry method simply does not work well in most situations, i.e. the method is unreliable and suffers from interference with numerous commonly used laboratory agents (see, e.g., Peterson, G. L, Anal. Biochem. 100:201–220 (1979), Peterson, G. L., Methods in Enzymology 91:95–119 (1983), and Stoscheck, C. M., Methods in Enzymology, 182:50–68 (1990), each of which is incorporated herein by reference). The difficulties in overcoming the drawbacks of the Lowry method are evidenced by the fact that despite a period of staggering growth in the biological sciences, the art of protein estimation remains limited to the Lowry method.

A. Long Sought And Unresolved Needs and Failures of Others

In 1979, Gary L. Peterson (Anal. Biochem. 100:201–220) published a review comparing the Lowry method with other protein assays. The review, which is herein incorporated by reference, included cross references to 127 publications describing the work of several hundred researchers. In his review, Peterson stated that "the principle disadvantage of this [Lowry] method is its lack of specificity." Peterson listed several hundred compounds and their derivatives that interfere with the Lowry method. Peterson also discussed numerous modifications of the Lowry method, including one of his own work, that he had tried; these methods achieved only limited success at best in improving the specificity and reducing interference by laboratory reagents.

The Peterson reference also provides an overview, as of 1979, of all other reported methods for protein determination, including biuret, Kjeldahl, U.V. absorption, alkaline hydrolysis-ninhydrin, protein fluorescence, turbidimetric, and protein-dye binding methods. All these methods suffer from a lack of specificity, i.e., large protein-to-protein variation, as well as poor sensitivity and complicated protocols. A relatively popular dye binding method by Bradford (Anal Biochem. 72:248–254 (1976), incorporated herein by reference) exhibits large protein to protein variation and interference with commonly used detergents. Other problems with the Bradford method are: (1) that the color produced is not stable due to acid precipitation of protein; and (2) that some proteins simply do not produce a linear standard curve, resulting in serious error. Peterson concluded that "all other methods seriously lack one or more of the following attributes: simplicity, sensitivity, or precision. All methods lack complete specificity (i.e., show large protein-to-protein variation and interference with common laboratory agents)."

After the publication of Peterson's review on the art of protein assay in 1979, those skilled in the art of protein assay continued trying to develop a simple, sensitive and highly specific protein assay, i.e., a protein assay independent of protein to protein variation and substantially free from interference by common laboratory agents. For example, various groups developed protein assays which involve spotting aliquots of protein solutions on support membranes.

Illustrative of this approach are articles by Kuno and Kihara (Nature 215: 975–976 (1967)), Bramhall et al (Anal. Biochem. 31:146–148 (1969)), and Minamide and Bamburg (Anal. Biochem. 190:66–70 (1990)), each of which are incorporated herein by reference. These articles describe methods of protein assay in which protein solution is spotted on filter paper. The resulting protein spots are stained with a protein dye, the dye, bound to the protein, is eluted from the filter paper, and finally the eluted dye is calorimetrically measured. All these methods are essentially variations of colorimetric methods and require the use of a standard protein and a calorimeter. In addition, they suffer from protein-to-protein variation because protein and dye interaction is not quantitative.

Kumar et. al (Biochem. Biophys. Res. Comm. 131:883–891(1985), incorporated herein by reference), have also described a protein assay in which protein is spotted on nitrocellulose paper, the resulting protein spots are stained, and protein concentration is then determined by measuring the color intensity of the protein spots. The Kumar method suffers from several drawbacks, including: complicated procedures, use of expensive instruments (e.g., a densitometer) and standards, lack of specificity, poor sensitivity, and protein-to-protein variation since the intensity of color of the protein spots depends on the tyrosine content of the protein(s) in the sample and the formation of a complex with starch. Furthermore, small protein fragments lacking tyrosine can not be assayed with this method.

These and other efforts were unsuccessful in developing a protein assay independent of protein to protein variation and substantially free from interference by common laboratory agents as demonstrated by reviews of the state of the art in 1983 and 1990 by Peterson and Stoscheck, respectively. In 1983, Peterson concluded that "unfortunately all [total protein assay] procedures that are relatively simple to perform and are usable in a variety of experimental situations do not give the same response with different proteins" (Peterson, G. L., Methods in Enzymology 91:95–119 (1983) (emphasis added), incorporated herein by reference). Similarly, in 1990, Stoscheck reviewed the sensitivity of various protein assays to common laboratory agents and the extent of protein to protein variation in these assays. (Stoscheck, C. M., Methods in Enzymology, 182:50–68 (1990), incorporated herein by reference.)

Applicant has also surveyed hundreds of papers on protein assay published until the filing of the parent patent application in 1995. Most of these articles are cited in the review articles already cited in this application. Most of these papers are either aimed at a specialized use of protein assay having limited application or describe attempts to improve existing methods. Unfortunately, they have all failed to achieve the attributes listed by Peterson and long sought by the artisan of protein assay.

In conclusion, the cited reviews establish how a large number of protein scientists over the years tried and failed to develop a reliable protein assay that is substantially protein specific, shows little or no protein-to-protein variation, is substantially free from interference by commonly used laboratory agents, is simple to perform, highly sensitive, and is easy to modify. Thus, there is a need for a protein assay with these attributes and which additionally does not require complicated procedures, running a set of known standards, or the use of colorimeters or densitometer. It is also desirable that such an assay be easily modified to allow its use in a variety of applications.

B. Historical landmark

The parent application (U.S. Ser. No. 08/370,685) of the instant application discloses a landmark development in protein chemistry, i.e., a protein assay that is substantially specific to protein with little or no protein-to-protein variation, substantially tolerates a wide variety of commonly used laboratory agents, is simple to perform, requires minimal use of instrumentation, sensitivity down to nanograms and produces substantially reliable results. As discussed above, such an assay has been sought by protein chemists for well over a century, during which thousands of scientists tried and failed to develop an assay having the above attributes. The novel protein assay described in U.S. Ser. No. 08/370,685 involves applying a small aliquot of a protein solution to a test strip or support membrane to produce a compact protein spot of a size that is substantially proportional to the concentration of protein in the protein solution. This proportional relationship allows the concentration of protein in a sample to be determined.

SUMMARY OF THE INVENTION

The present invention provides a method, device and kit for determination of total protein concentration, or protein assay, in a sample. As used herein, protein refers to proteins in general and is not limited to proteins having any particular characteristics. Total protein means all the protein that is present in a sample. Thus, the protein assay of the invention is useful to determine total protein concentration in samples having only one protein as well as samples having a mixture of different proteins. It is not necessary to know anything about the primary, secondary or tertiary structure of the protein(s) in the sample to practice the invention.

The protein assay of the method and kit disclosed herein is substantially protein-specific, thus the sample may contain nonproteinaceous biomolecules commonly present in biological samples, e.g., nucleic acids, carbohydrates, and lipids. In addition, the protein assay of the invention is substantially free from protein-to-protein variation and interference by commonly used laboratory agents, such as detergents, drugs, urea and other denaturing agents, dyes, reducing agents, chelating agents, various organic and inorganic buffers and so forth. The protein assay is reliable and simple to perform and does not require the use of any complicated instrument. In addition, the method of the instant invention is simple to modify for extraordinary situations and has sensitivity as low as 1–5 $\mu$g/ml.

Accordingly, the invention provides a method for determining total protein concentration in a protein solution, which comprises: applying the protein solution to a porous protein-support capable of retaining the protein in the form of a protein spot having a size that is proportional to the protein concentration, when the protein contacts the protein-support in the presence of a detergent and at least one of a salt or an acidic agent; measuring the size of the protein spot produced on the protein-support; and comparing the size of the protein spot with a standard.

The present invention also provides a device, hereinafter referred to as a protein gauge, for determining an unknown amount of total protein in a substantially circular protein spot on a protein-support, which comprises a display showing a substantially linear relationship between spot diameter and protein amount for at least two substantially circular standard spots containing known amounts of protein produced on the protein-support.

The invention is also directed to a kit for determining the concentration of total protein in a protein solution, which comprises: a porous protein-support for retaining the protein from the protein solution applied to the protein-support, wherein the protein-support is capable of retaining the protein in the form of a substantially circular protein spot having a diameter that is proportional to the protein concentration when the protein contacts the protein-support in the presence of a detergent and at least one of a salt or an acidic agent; a protein gauge for determining an unknown amount of protein in the protein spot, wherein the gauge shows a substantially linear relationship between the diameter of the protein spot and the amount of protein in the spot; a dilution solution for preparing the protein solution from a sample to be measured; and preferably, a reagent solution for visualizing the protein spot on the protein-support.

The invention will be better understood by reference to the following detailed description of preferred embodiments of the invention and the drawings that form part of this specification.

BRIEF DESCRIPTION OF THE DRAWINGS

FIG. 5(I–III) shows three plots of the substantially linear relationship between the amount of protein per spot and the diameter of protein spots produced on a protein-support in accordance with the invention, with each plot showing a different range of protein amounts.

DESCRIPTION OF THE PREFERRED EMBODIMENTS

Determining the concentration of total protein in a protein solution in accordance with the invention comprises applying the protein solution to a porous protein-support in the presence of a detergent and at least one of a salt or an acidic agent to produce a protein spot whose size is proportional to the amount of protein in the spot; measuring the size of the protein spot on the protein-support; and comparing the size of the protein spot with a standard.

The protein-support is capable of retaining the protein in the form of a substantially uniform protein spot having a size that is proportional to the total protein concentration in the solution when the protein contacts the protein-support in the presence of a detergent and at least one of a salt or an acidic agent. The protein spot may have any shape whose size is capable of being measured quantitatively. For example, the protein spot may have a circular, rectangular, or any other geometric shape for which well-known size measurements exist, provided the applied protein is spread substantially uniformly throughout the shape of the spot. The spot size measured may include, but is not limited to, diameter, area, circumference, density, or volume of the shape produced. Preferably, the protein-support is capable of producing protein spots that are substantially circular in shape having diameters that are substantially proportional to the concentration of total protein in the solution.

The protein-support may comprise a porous membrane such as nitrocellulose, nylon and other types of protein binding membranes well-known in the art. The pore size of the protein-support is large enough to provide sufficient capillary wicking action to produce substantially uniform protein spots whose sizes vary proportionally with protein concentration to an extent that can be reliably measured. Preferably, the pore size is larger than 0.05 µm. More preferably, the pore size of the protein-support is 0.2 µm or larger. Most preferably, the protein-support has a pore size of approximately 0.45 µm.

Preferably, the protein-support comprises a nitrocellulose membrane having a binding capacity for the standard reference protein, bovine serum albumin (BSA), of at least 100 µg/cm$^2$.

The protein-support is preferably large enough to allow complete diffusion of the protein solution applied to it without the protein solution reaching the edges of the protein-support. For example, a 1 µl solution applied to a protein-support according to the invention would generally spread 6–7 mm outward from the point of application; therefore, the protein-support is preferably wider than 7–8 mm so that the spreading solution does not reach its edges.

The volume of protein solution applied to the protein-support is preferably maintained constant, at about 1–10 µl per spot. Most preferably, the volume of protein solution applied to the protein-support is 1–5 µl. The protein solution is preferably applied to the protein-support in such a manner that the solution diffuses slowly into the protein-support, i.e., preferably through capillary action; forcibly expelling the protein solution onto the protein-support is not recommended.

To promote formation of protein spots that are proportional to the concentration of total protein in the protein solution applied to the protein-support, the protein contacts the protein-support in the presence of a detergent and at least one of a salt or an acidic agent. Preferably, both a salt and an acidic agent are used. As used in the invention, detergent means both ionic and non-ionic detergents including, but not limited to, sodium dodecyl sulfate (SDS), Triton X-100, NP40, Tween-20, and other non-polar agents. Salts which are operable in the invention include, but are not limited to, sodium, potassium, and other salts. Examples of the acidic agent include, but are not limited to, acetic acid, phosphoric acid, trichloroacetic acid, and citric acid.

The presence of a detergent and at least one of a salt or acidic agent may be provided by impregnating the protein-support with one or more of these reagents and/or adding one or more of these reagents to the protein solution before it is applied to the protein-support. The concentrations of detergent, salt and/or acidic agent are such that there is a substantially linear relationship between the size of the protein spot produced and the amount of protein in the spot. Preferably, this linear relationship exists for protein spots having between 0.05 µg to 5 µg protein, and most preferably, for spots having between 0.01 µg to 5 µg protein.

In one preferred embodiment of the invention, the concentrations of detergent, salt and/or acidic agent in the protein-support and/or the protein solution are those which allow the protein solution, in the combined presence of these agents, to form a protein spot on the protein-support whose size changes by about two-fold or higher when the protein concentration changes about ten-fold. For example, if 1 µl of a protein solution containing 0.05 mg/ml protein produces a protein spot of 1–2 mm in diameter in the presence of a particular combination of detergent, salt and/or acid, then 1 µl of a solution containing 0.5 mg/ml will produce a protein spot of approximately 2–4 mm in diameter in the presence of that particular combination. The combination of the concentrations of detergent, salt and/or acid which achieves this preferred spot forming property is referred to as the spot-sizing combination.

More preferably, the spot-sizing combination comprises those concentrations of detergent, salt, and/or an acidic agent which allow the smallest spot produced by 1 µl of a protein solution to have a diameter of approximately 1–2 mm. Most preferably, the smallest measurable spot produced in the presence of the spot-sizing combination corresponds to the lowest detectable protein concentration for a sample.

The spot-sizing combination will vary depending on the protein spot-forming characteristics of different batches and/or types of membranes used as the protein-support, and may also vary due to any effect on protein spot formation by various chemical agents originally present in the protein sample, e.g., buffering agents, denaturants, salts, and detergents. Thus, for optimal results, the spot-sizing combination for a particular protein-support and protein sample is derived by adjusting the concentrations of detergent, salt and/or acid in the protein-support and/or the protein solution until substantially uniform protein spots of the preferred size distribution are achieved. The skilled artisan will appreciate that such adjustments are routine.

It should be evident to the skilled artisan that an approximate two-fold change in protein spot diameter (i.e., by changing the protein concentration by ten-fold) will provide a measurable difference in the diameters of protein spots containing different amounts of protein. The skilled artisan will also appreciate that any condition that results in changes in protein spot diameter of less than two-fold can still be used in the invention as long as the changes in protein spot diameter are measurable without requiring the use of complicated instruments.

Another preferred embodiment of the invention is based on the discovery that when some types of membranes are used for the protein-support, i.e., a nitrocellulose with a protein binding capacity of 300 $\mu g/cm^2$ for BSA (pore size 0.45 $\mu$m), increasing salt concentration in otherwise identical protein solutions, i.e., having the same protein concentration, results in a rather rapid corresponding decrease in protein spot diameter up to a particular concentration of salt, and that above this concentration there is a range of salt concentrations within which little to no further reduction in spot size occurs with increasing salt concentration. Any salt concentration within this range has approximately the same affect on protein spot size and is thus referred to as a saturating salt concentration. Therefore, when a saturating salt concentration is present, the size of the protein spots produced will not be affected by the presence of salt in the original protein sample and will be substantially proportional to protein concentration. Outside the range of saturating salt concentrations there is a certain higher salt concentration at which protein spot formation is deleteriously affected due to the precipitation of the protein and detergent.

The range of saturating salt concentrations will vary depending on the protein spot-forming characteristics of different batches and/or types of membranes used as the protein-support, and will need to be empirically determined for each batch and/or type of membrane to achieve optimal results. This type of empirical determination would be considered routine by those skilled in the art.

The protein spots produced on the protein-support may be detected either by physical or chemical means. Such means include methods for detecting proteins bound to a membrane which are currently known to those skilled in the art or any such methods developed in the future. For example, protein spots may be detected by staining the protein-support with protein dyes such as Coomassie blue or silver dyes. Alternatively, the protein spots may be detected with the aid of chemically coupled reactions such as chemiluminescent reactions or the protein iodination linked starch reaction (i.e. iodine-starch reaction). Most preferably, the protein spots are detected with the iodine-starch reaction, as described in the method section. This step is not necessary when assaying colored protein, protein coupled with a dye, or when a colored protein is used as an internal standard in the assay.

Before applying the protein solution to the protein-support, the protein solution is preferably mixed with a dilution solution. The dilution solution is preferably acidic in nature and may contain a spot-sizing combination of detergent, salt, and/or an acidic agent. If a salt is present in the dilution solution, its concentration is preferably less than 1 M, and more preferably the concentration of salt in the dilution solution is about 0.05–500 mM. Most preferably the dilution solution contains a saturating salt concentration. Preferably, the salt used in the dilution solution is a sodium salt, e.g., NaCl.

The dilution solution may also contain a predetermined concentration of an internal standard protein. The internal standard protein may be pre-stained, thereby allowing visualization of protein spots without any need for performing an iodine-starch reaction or other means of detecting the protein spots. As would be evident to those skilled in the art, when an internal standard protein is added to the dilution solution, the concentration of total protein in the original, undiluted sample, is calculated by subtracting the concentration of internal standard from the concentration of total protein in the diluted protein solution as determined by the method of the invention.

In order to improve the accuracy of the protein assay method and overcome interference by chemical agents present in a protein sample, preferably more than one protein spot is produced from each test sample. For example, a plurality of spots may be produced from one protein solution and the protein concentration in the solution is determined either from the average size of at least two spots or by averaging the concentrations determined from at least two spots.

Preferably, the concentration of total protein in a sample is determined from measuring the sizes of a plurality of protein spots produced from serial dilutions of the sample using dilution solution. The serial dilutions are preferably carried out in such a way that each successive dilution is 2-, 3-, or 5-fold more diluted than the previous dilution. Protein solution from each dilution is applied to the protein-support and the protein concentration in the sample is preferably determined by averaging the concentration determined from at least two of the protein spots. Preferably, each spot represents a different dilution of the sample in dilution solution.

When selecting which protein spots to measure for determining protein concentration, substantially uniform protein spots of higher-fold dilutions are preferred over nonuniform spots or protein spots of lower-fold dilutions. When measuring the diameters of the selected protein spots, each spot is preferably measured more than one time and each time a different cross-sectional diameter is preferably measured.

Once the size of a sample protein spot is measured, the amount of protein in the sample spot is determined by comparing the size of the spot to a standard. The standard shows a proportional relationship between known, but different amounts of a standard protein contained in a plurality of standard spots and the spot sizes thereof. The standard protein may be any type of soluble protein. Preferably, the standard protein contains tyrosine so that the standard protein spot may be detected with the iodine-starch reaction. Most preferably, the standard protein is bovine serum albumin (BSA). It will be understood by those of ordinary skill in the art that the standard spots are shaped similarly as the sample spots and that the type of size measurement, e.g., diameter, area, etc., is the same for the standard spots and sample spots.

Preferably, the standard is a protein gauge which displays a substantially linear relationship between spot diameter and protein amount in substantially circular protein spots produced from protein solutions of known concentration in accordance with the invention. For example, the protein gauge may be in the form of a table or graph which relates the diameter of protein spots to the known amounts of protein in those spots. The protein gauge may also include means for measuring the size of the protein spots.

The concentration (i.e., $\mu g/\mu l$) of total protein in the original sample is calculated by dividing the amount of protein (i.e., $\mu g$) in a measured spot, as determined by comparing the spot size to a standard, by the volume of protein solution (i.e., $\mu l$) applied to form the spot and then multiplying by the dilution factor, if any, for that protein spot.

Dilute solutions, i.e., less than 0.5 mg/ml, are preferably assayed using a dilution solution containing a saturating concentration of a salt and applying at least 1–5 $\mu l$ of protein solution to the protein-support. Alternatively, such dilute protein solutions may be assayed by adding a predetermined amount of an internal standard protein and subtracting the concentration of the internal standard from the concentration determined from measuring the protein spot(s).

In another embodiment of the invention, very dilute solutions, i.e., less than 5 $\mu g/ml$, are assayed by applying 1 $\mu l$ aliquot of serial dilutions of the sample solution to the protein-support. To determine the concentration of the undiluted sample, the dilution factor for the last visible protein spot is multiplied by the limit of detection of the method. This method of determining total protein concentration in very dilute protein solutions is illustrated in Example 7.

Another object of the present invention is to provide a protein gauge useful for determining the amount of protein contained in protein spots produced according to the above described method. The protein gauge comprises a display showing a substantially linear relationship between spot diameter and protein amount for at least two substantially circular standard spots containing known, different amounts of a standard protein. Preferably, the display shows a substantially linear relationship between spot diameter and protein amount for standard spots containing from about 0.025 $\mu g$ to about 5.0 $\mu g$ protein. More preferably, the display shows spot diameters ranging from about 0.5 mm to about 7 mm for standard spots containing from about 0.01 $\mu g$ to about 5.0 $\mu g$ protein, respectively.

The substantially linear relationship between size and protein amount for the standard spots may be the result of any type of chemistry currently known or developed in the future. Preferably, the chemistry producing this relationship is the method described above, i.e., the standard protein spots are produced in the same manner as the sample protein spots.

Figure 3:
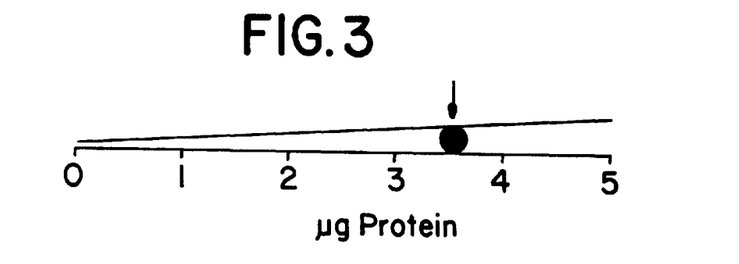
FIG. 3 shows a first embodiment of a protein gauge based on the plot of FIG. 2 and illustrates how it is used for determining the amount of protein in protein spots produced on a protein-support in accordance with the invention.
Figure 6:
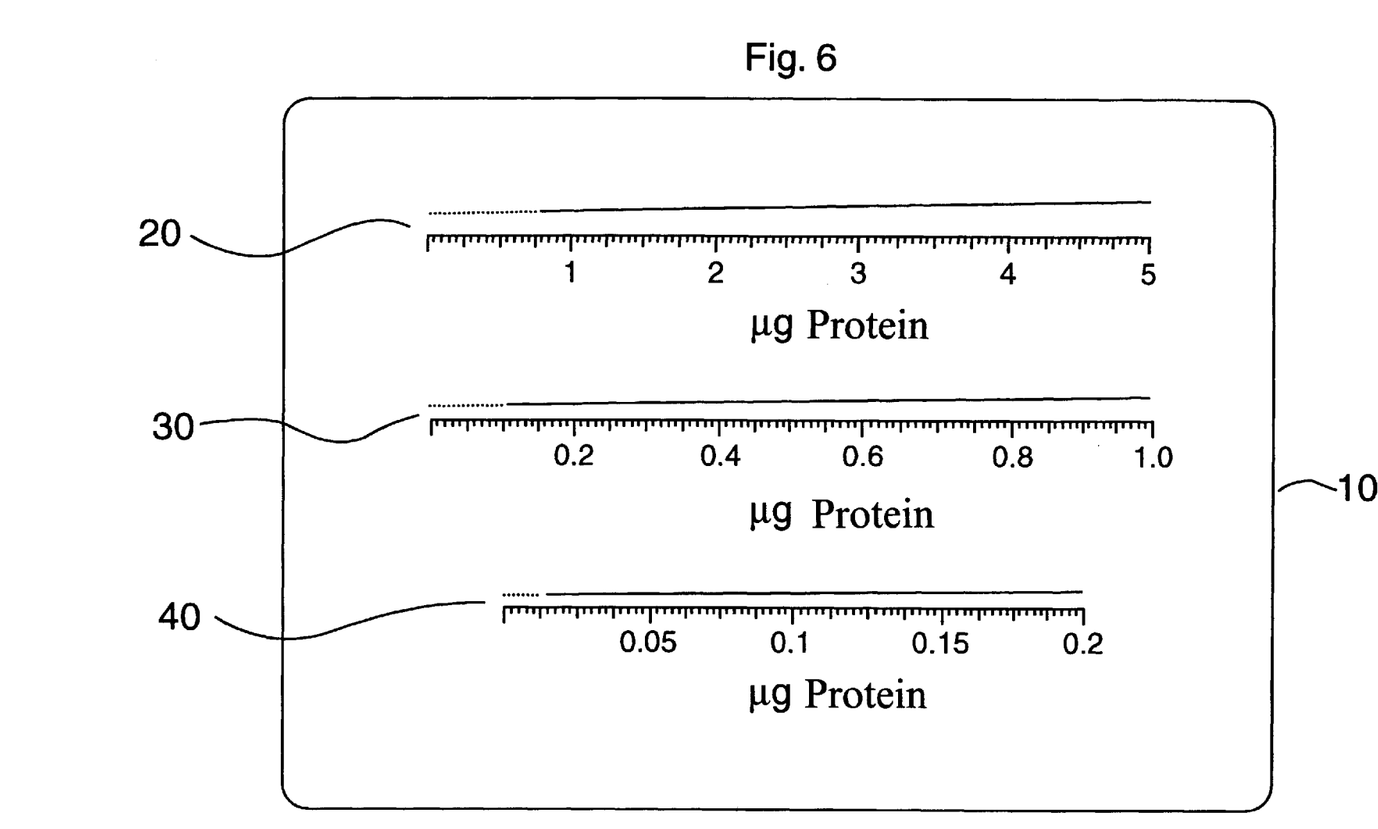
FIG. 6 shows a third embodiment of the protein gauge which is derived from the plots of FIG. 5.

In the preferred embodiment, the display of the protein gauge has means for simultaneously measuring the diameter of the protein spot and comparing this measurement to the substantially linear relationship exemplified by the display. As shown in FIG. 3, the means for simultaneously measuring and comparing preferably comprises at least one wedge-shaped display composed of first and second converging linear members, at least one of the members being graduated, and the angle of convergence between said members delineates the substantially linear relationship between spot size and protein amount, and the graduated member having at least one reference mark representing a protein amount or spot diameter. The reference mark may comprise numerals, symbols, letters, words, or any other designation whose relationship with the represented amount of protein or spot diameter is known. Preferably, the angle of convergence has a degree defined by a distance between the first and second linear members of about 1 mm at 0.0125 $\mu g$ of protein and about 3 mm to about 7 mm at 5 $\mu g$ of protein. The protein gauge may have one display showing protein amounts in a range from 0.01 $\mu g$ to 5 $\mu g$, or the gauge may have multiple wedge-shaped displays showing protein amounts in intermediate ranges between 0.01 $\mu g$ and 5 $\mu g$ as shown in FIG. 6. Gauges with multiple displays are useful for more precise determinations of protein-concentration over a wide range of protein concentration.

The protein gauge having at least one wedge-shaped display is made by measuring the diameters of at least two standard protein spots containing known, but different amounts of a standard protein, with the spots preferably being produced on a protein-support according to the above described method, and plotting the diameter versus protein amount, or vice versa, for each spot on an X-Y graph. The linear section of the curve generated by connecting each point on the plot that corresponds to a standard protein spot defines one of the two converging linear members of the display and has a slope which defines the angle of convergence between these converging members. The other linear member of the display is defined by the X or Y axis, and is preferably defined by the axis representing protein amounts. Preferably, the display is then transferred to a transparent sheet material, allowing the display to be placed immediately over the protein spot or spots to be measured, as shown in FIG. 3.

The protein gauge is used by placing a visible protein spot containing an unknown amount of protein on the wedge-shaped display, moving the spot along the wedge until the top and bottom boundaries of the spot just meet the interior edges of the linear members of the wedge, and then reading the spot diameter and/or protein amount from the point on the graduated linear member located immediately above or beneath the center of the circular spot. Preferably, if the protein gauge is transparent, the gauge is placed on top of the protein-support containing the protein spot to be measured and maneuvered until the display is directly over the protein spot as described above and shown in FIG. 3.

Figure 4:
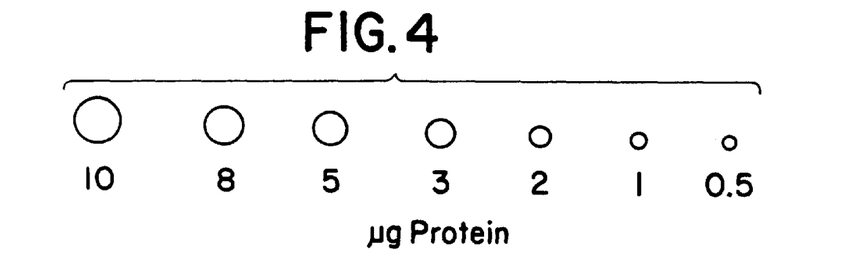
FIG. 4 shows a second embodiment of the protein gauge which contains a series of circular measuring means.

Alternatively, the means for simultaneously measuring and comparing comprises a plurality of circles as shown in FIG. 4, with the circles having diameters that correspond to the diameters of protein spots containing known, but different amounts of a standard protein, with the spots preferably being produced according to the method of the invention. The amount of protein in a spot being measured is estimated by comparing the diameter of the sample protein spot with the diameter of the circles.

The protein gauge may also have variable measuring means for measuring the sizes of protein spots. The variable measuring means adjusts so that different settings are used to measure different spot sizes and includes, but is not limited to, a calliper gauge.

Other types of protein gauges may be prepared as long as the protein gauge can be used for measuring the size of protein spots and has a display which shows a substantially linear relationship between protein amount and the size or diameter of protein spots. For example, the display may be a table relating the size or diameter of protein spots with corresponding protein amounts.

Another object of the invention is to provide a kit for determining the concentration of total protein in a protein solution. The kit comprises: a porous protein-support for retaining the protein from the protein solution applied to the protein-support, wherein the protein-support is capable of retaining the protein in the form of a substantially circular protein spot having a diameter that is proportional to the protein concentration when the protein contacts the protein-support in the presence of a detergent and at least one of a salt or an acidic agent; a protein gauge for determining an unknown amount of protein in the protein spot, wherein the gauge shows a substantially linear relationship between the diameter of the protein spot and the amount of protein in the spot; a dilution solution for preparing the protein solution from a sample to be measured; and preferably, a reagent solution for visualizing the protein spot on the protein-support.

The invention will be further explained and illustrated by the following nonlimiting examples.

EXAMPLES

Materials and Methods

Protein-Support

Strips of the protein-support, 8 mm×80 mm, were used in all examples. Unless otherwise indicated, the protein-support was prepared from a nitrocellulose membrane having a pore size of 0.45 μm and binding capacity of 100 μg BSA/cm$^2$.

In some experiments, the protein-support was impregnated with an acidic agent prior to application of the protein solution. This acid impregnation was accomplished by soaking a membrane in a solution of the acidic agent for 5 min. and then air drying overnight, e.g., 12 hrs.

Protein Solutions

Unless otherwise indicated, a standard 10 mg/ml bovine serum albumin (BSA) solution in water was used as the protein solution in these examples. Several separate dilutions were prepared from the 10 mg/ml BSA solution using water, unless otherwise specified, and a 1–5 μl aliquot from each dilution was applied to the protein-support. In some experiments, the standard BSA solution was diluted with one of the following dilution solutions:

Reagent D: 0.05% Triton X-100, 0.05 M NaCl, and 5% acetic acid;

Reagent E: 0.1 M NaCl, 5% acetic acid, and 0.1% to 1% SDS;

Reagent F: 0.075 M NaCl, 5% acetic acid, 1% SDS and 0.05% Triton X-100; or

Reagent G: 5% acetic acid, 0.1 M sodium chloride, 1% SDS, and 0.05% Triton X-100.

Application of Protein Solution to Protein-Support

The protein solution was applied to the protein-support with a commercially available pipettor using a 0.1–10 μl commercially available plastic pipet tip with an outer diameter (O.D.) of around 0.6–0.7 mm. The pipet tip was first wet with the protein solution by pulling 2–5 μl of the solution into the tip and then ejecting this back into the solution; this process was performed once or twice. The volume on the pipettor was then adjusted to 1–5 μl and the protein solution was pulled into the tip. After making sure there was no air bubble trapped in the tip, the pipet tip was removed from the solution while touching the tip to the wall of the solution container to remove any drop of solution hanging from the tip.

The pipet tip containing the 1–5 μl aliquot of protein solution was positioned vertically over the protein-support and then lowered until the pointed end of the tip just touched the protein-support. When applying the protein solution to the protein-support, care was taken to allow the solution to diffuse slowly out of the pipetor tip into the protein-support rather than forcing the protein solution out of the tip with the pipetor plunger. Care was also taken to not move the pipet tip during the diffusion process. The application of protein solution in this manner normally takes 15–20 seconds. The protein-support was allowed to air dry 1–2 minutes and then treated to detect protein spots, as described below.

Detecting Protein Spots

The spots produced in the following examples were detected with the iodine starch reaction, using the following reagent solutions:

Reagent A: 1% KI (Potassium Iodide) solution in 1 n HCl;

Reagent B: 0.5% Chloramine T solution in distilled water; and

Reagent C: 1% soluble potato starch solution in water.

The protein-support containing the dried protein spots was incubated for 2 min in a 10-fold dilution of Reagent A (10 ml). Then Reagent B (1 ml) was added to the container holding the protein-support and diluted Reagent A (the final concentration of Chloramine T in the mixed Reagents A & B solution was 0.05%) and incubation continued for an additional 2 min. After the incubation in Reagent A & B, the protein-support was transferred to a 10-fold diluted solution of Reagent C and incubated in the dark and cold, eg., about 4° C. until the protein spots were visible, about 3–5 min.

The diameters of the protein spots were measured before the protein-support was completely dry, i.e., within five minutes of removing the protein-support from Reagent C, as the color begins to fade around the edges of the spot once the protein-support is completely dry. Alternatively, a photocopy of the protein-support was made before the protein-support dried completely and the photocopy was used to measure the protein spots.

Example 1

Effect of Detergent, Salt and Acid on Protein Spot Formation

In one experiment, the standard 10 mg/ml BSA solution was diluted in water, 1% SDS (sodium dodecylsulfate, an ionic detergent), or Triton X-100 (a non-ionic detergent) to give BSA concentrations of 0.05 mg/ml to 5.0 mg/ml BSA. A 1 μl aliquot from each dilution was applied to a protein-support (the protein-support was not treated with trichloroacetic acid, TCA or any other acid). After air drying, the spots on the protein-support were detected according to the iodine-starch method described above. It should be noted that when assaying colored proteins, or protein coupled with a dye, or when colored protein is used as an internal standard, there is no need to treat the protein-support with a spot detecting reagent as solutions containing such proteins produce visible spots.

The protein in the solution diluted with water substantially spread with the water in the solution and produced spots almost equivalent to the water marks. The protein in solutions diluted with 1% SDS or 1 % Triton X-100 spread in a wider area than when diluted with water. The diameter of a protein spot produced from a 1.0 mg/ml BSA solution was almost similar to the diameter of a protein spot produced from the 5 mg/ml BSA regardless of whether the solution had been diluted in water or detergent. As the concentration of protein decreased, the protein spots became fainter in color. The concentration of protein could be estimated by measuring the color intensity of the protein spots.

In another experiment, a TCA-impregnated nitrocellulose membrane (binding capacity 5 of 100 μg/cm$^2$) was used as the protein-support. Protein solutions containing 0.01 mg/ml to 5 mg/ml BSA were prepared in Reagent E, a dilution solution containing 1% SDS, 5% acetic acid and 0.075 M NaCl. A 1 μl aliquot from each dilution was applied to the membrane and the spots detected as described above.

Figure 1:
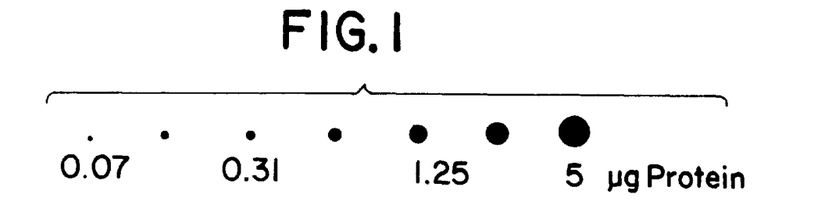
FIG. 1 shows an actual print of protein spots produced by applying protein solutions of various concentrations to a protein-support in accordance with the invention; the print illustrates the proportional relationship between the amount of protein in a protein spot and the diameter of the protein spot.
Figure 2:
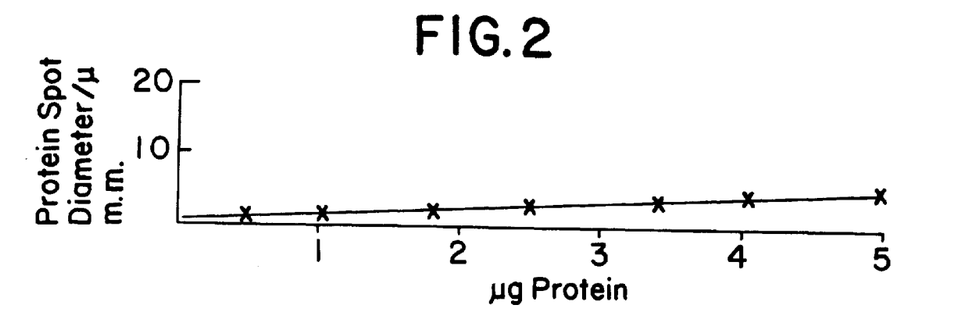
FIG. 2 shows a plot illustrating the substantially linear relationship between the diameter (mm) of the protein spots and the amount of protein (µg) in protein spots produced on a protein-support in accordance with the invention.

The protein spots produced from solutions in Reagent E were much tighter and more compact than spots produced from protein solutions prepared in only water or detergent;

significantly, the protein did not spread with the water in the solution. Protein solutions with higher protein concentrations produced larger spots than protein solutions with lower protein concentrations (see FIG. 1). The diameter or size of protein spots was substantially proportional with protein amount for spots containing more than 0.0125 µg protein. Spots containing less than 0.0125 µg protein were almost identical in size and too small for measurement; however, the color intensity of the spots continued to decrease with decreasing protein concentration.

Example 2

Effect of Membrane Type on Protein Spot Formation

Membranes obtained from various commercial sources were tested for their suitability as the protein-support, i.e., having the capability to retain protein in the form of a substantially uniform protein spot whose size is substantially proportional to the amount of protein. The membranes tested had relatively high protein binding capacities, i.e., 75–400 µg/cm$^2$ with pore sizes of 0.05 µm to 0.45 µm and included protein binding membranes such as nitrocellulose, nylon, and polyvinylidene diflouride (PVDF).

Protein solutions containing 2.5 mg/ml protein (BSA) were prepared in deionized water, 1% SDS, 1% Triton X-100, 0.1 M NaCl, or 5% acetic acid. Serial dilutions of each protein solution were prepared by making each successive dilution a 3-fold dilution in their respective solutions (i.e., solutions containing water, 1% SDS, 1% Triton X-100. 0.1 M NaCl or 5% acetic acid as specified above). Other serial dilutions of the 2.5 mg/ml BSA in water were made using dilution solutions containing different concentrations and combinations of the above reagents. A 1 µl aliquot of protein solution from each dilution was applied to various membranes. The membranes were then treated with the iodine-starch reaction to detect the protein spots.

It was discovered that protein spot forming properties of protein binding membranes varied considerably among the tested membranes. One factor which affected spot formation was the pore size of the membrane; the larger the pore size the more easily and uniformly the protein solution diffused into the membrane, resulting in more uniform and more circular protein spots. Membranes with a pore size of 0.05 µm produced much smaller protein spots than membranes having a 0.45 µm pore size. In fact, the protein spots produced on membranes having a 0.05 µm pore size were so small (about 1 mm) and compact for protein solutions made in water that there was very little difference in the size of protein spots produced from solutions having between 0.03 mg/ml to 2.5 mg/ml BSA concentration.

Another factor that influenced the formation of protein spots on the membrane is the protein binding capacity of the membrane. Membranes with higher protein binding capacity produced smaller protein spots than membranes with lower binding capacity.

Yet another factor that influenced the formation of protein spots was wetability of the membrane. Membranes that wetted easily allowed protein solution to diffuse easily and spread uniformly, resulting in uniform and circular protein spots. PVDF membranes generally were very difficult to work with since protein solution applied to dry PVDF membranes did not easily diffuse into the membrane.

In the presence of a detergent, protein solution applied to the various membranes spread widely; here again, the size of protein spots varied significantly from membrane to membrane, with the size being dependent on pore size, binding capacity and other unknown factors.

It was also discovered that the presence of a salt or an acid in a protein solution significantly influenced the size of protein spots produced on the various membranes. Both acid and salt have the property to significantly reduce the size of protein spots. With some membranes, when protein was applied in the presence of a salt, the protein spots were very small (i.e., diameters of 1–2 mm), even when produced from solutions of higher protein concentrations, i.e., 2.5 mg/ml; in these cases, the range of protein concentrations that could be assayed was significantly reduced.

Furthermore, the influence of salt and acid concentration was not uniform for the membranes tested. For each membrane, the response to a given concentration of salt, acid, or combination of salt and acid was different. For example, either at 0.05 M NaCl or 2% acetic acid, each membrane tested produced protein spots of different diameters from the same protein solution. In fact, the variation in spot formation properties of protein binding membranes is so prevalent and considerable that it was discovered that membranes having identical specifications obtained from the same manufacturing source showed significant batch to batch variations. Manufacturing processes and so called inert binding materials used in the manufacturing of various protein binding membranes also significantly influenced spot formation properties of these membranes.

When protein solution was diluted in a dilution solution containing 5% acetic acid, 0.1 M sodium chloride, 1% SDS, and 0.05% Triton X-100 (Reagent G), it was discovered that the spot formation was very different when compared with spots produced from protein solutions prepared in the presence of any one of the individual Reagent G ingredients. Furthermore, at a given protein concentration in Reagent G, each membrane produced protein spots of a different diameter. It was, however, possible to adjust the concentration of detergent, salt and/or acidic agent in a protein solution such that a given protein concentration produced substantially identical protein spots and/or protein spots of a predetermined diameter on most types of protein binding membranes.

The above experiments established that the spot formation properties of various protein binding membranes are so different that they cannot be used as a protein-support for protein assay without significant chemical intervention. Furthermore, it should also be considered that protein solutions, depending on their source, may also contain various salts, buffering agents, detergents and so forth. Thus, for the most reliable protein assay, it is necessary to carefully establish the concentrations of detergent, salt and/or acid at which a particular membrane will have predetermined spot formation properties, i.e., produce protein spots of a predetermined diameter from solutions of a given protein concentration. The combination of the concentrations of detergent, salt and/or acid which achieves this predetermined spot forming property is referred to as the spot-sizing combination, and was defined above.

Example 3

Effect of Acid on Protein Spot Formation

In another experiment, the effect of different acids in spot formation was investigated. It was discovered that treating a protein binding membrane with an acidic agent as described above enhanced the protein binding capacity of the membrane and affected the size of protein spots produced on the membrane. Specifically, at a given concentration of detergent and salt, as the concentration of an acidic agent in the protein-support or dilution solution increased (e.g., from 1% to 5% acetic acid), the size of protein spots decreased. Various acidic agents, including acetic acid, TCA, citric acid, and phosphoric acid, showed comparable results.

The effect of acid on the spot formation property of a membrane was very substantial when applying less concentrated protein solutions (i.e., less than 0.5 mg/ml) which contained a non-ionic detergent or when protein solution contained SDS. When an acidic agent was not present in either the membrane or in the protein solution, the protein had a tendency to spread widely, producing very diffuse protein spots. However, when the same protein solutions were applied to an acid-impregnated membrane, the protein spots produced were compact and substantially uniform. Different acidic agents similarly influenced the spot formation property of the membrane, either when the acidic agent was added to the protein solution or when it was added to the membrane before applying the protein solution.

The effect of the presence of an acid in the protein-support on protein spot formation was further investigated by determining whether this effect was the same for protein solutions having alkaline pHs. When 1 $\mu$l of a protein solution containing 0.1 M Tris-HCl, pH 8.3 was applied to a nitrocellulose membrane impregnated with 5% TCA, the size of the protein spot produced was larger than would be expected for a protein solution made in water. It is suspected that the alkaline protein solution neutrilized the acid in the membrane. When this protein solution was acidified (to a pH of about 2–3) by adding a small volume of acetic acid, before applying the solution to the protein-support, the protein spots had the expected size. This experiment suggested that maintaining an acidic pH in the protein solution was required for maintaining the effect of the acidic agent in the membrane on protein spot formation.

Example 4

Effect of Detergent Concentration on Protein Spot Formation

The effect of detergent on the protein spot forming property of an acid-impregnated protein-support was investigated in an experiment using a nitrocellulose membrane (pore size of 0.45 $\mu$m and protein binding capacity of 100 $\mu$g/cm$^2$) impregnated with 5% trichloroacetic acid (TCA). A BSA solution was prepared in 1% SDS and then serially diluted with a dilution solution containing 5% acetic acid and 0.1 M NaCl. A 1 l aliquot from each dilution was applied to the acid-impregnated membrane. Under these conditions, 0.05 mg/ml to 2 mg/ml BSA solutions produce very small and compact spots of approximately 1–2 mm in diameter. However, when BSA solutions having 0.05 mg/ml to 2 mg/ml BSA were prepared with dilution solutions containing from 0.1% to 2% SDS, as well as 5% acetic acid and 0.1 M NaCl, the protein spots on the acid-impregnated membrane had diameters of about 1 to 6 mm.

Additional experiments established that for protein solutions diluted with 5% acetic acid and 0.1 M NaCl, spot formation was deleteriously affected if the concentration of SDS in the diluted protein solution dropped below 0.1%, i.e., the protein spots were very small and their sizes were not proportional to the amount of protein they contained. Conversely, when the SDS concentration in these diluted protein solutions was between 0.1% SDS and about 2%, the protein spots produced had sizes that were substantially proportional to protein amount per spot.

Thus, it was discovered that, at a given acid and salt concentration, the presence of a detergent within a defined range was critical to produce a protein spot having a size proportional to the protein concentration when the protein-support was an acid-impregnated nitrocellulose membrane (pore size of 0.45 $\mu$m and protein binding capacity of 100 $\mu$g/cm$^2$).

Example 5

Effect of Salt Concentration on Protein Spot Formation

In an experiment similar to the one described in Example 4, the effect of varying NaCl concentration on the spot forming property of an acid-impregnated protein-support was investigated. The protein sample was prepared in 1% SDS and the concentrations of acid and detergent in the dilution solution were maintained constant at about 5% acetic acid and 1% SDS, respectively, and a nitrocellulose membrane (pore size of 0.45 $\mu$m and binding capacity of 100 $\mu$g/cm$^2$) was impregnated with 5% TCA, as described above. It was discovered that NaCl concentrations below 0.05 M had no measurable effect on spot formation, i.e., protein spots containing different protein amounts had similar diameters. However, at 0.1 M to 0.2 M NaCl, the protein spots showed a linear relationship between spot diameter and protein amount. At NaCl concentrations above 0.5 M, this linear relationship suddenly collapsed, i.e., spots produced from 0.05 to 5 mg/ml protein solutions were all about 1 mm in diameter. Other salts showed comparable results. These effects of salt concentration on protein spot formation were not uniform for the tested membranes.

In a different experiment, a high binding capacity nitrocellulose membrane (300 $\mu$g BSA/cm$^2$, pore size of 0.45 $\mu$m) was used for the protein-support. The membrane was not impregnated with any acid. The concentrations of detergent and acid were maintained constant in the dilution solution at 1% SDS and 5% acetic acid, respectively, while the concentration of salt was varied from 0.0 to 0.3 M NaCl. A standard 0.5 mg/ml BSA solution was prepared in each dilution solution and 1 $\mu$l aliquot (containing 0.5 $\mu$g) were spotted on the protein support. It was discovered that between 0.0 to 0.08 M NaCl the diameter of protein spots dropped rapidly from 6.2 mm (at 0.0 M NaCl) to 3.0 mm (at 0.08 M NaCl). Thereafter, the drop in spot diameter was not significant, i.e., when NaCl concentration increased from 0.08 M to 0.3 M, the spot diameter decreased by a total of only 0.25 mm. Thus, at 0.08 M NaCl, the maximum effect of salt in reducing the spot diameter had been reached and any NaCl concentration within the tested range (0.08 M to 0.3 M) would be a "saturating salt concentration" as defined above for the particular combination of membrane, detergent and acid used in this experiment.

This saturating effect of salt concentration was even more apparent at lower protein concentrations. When the protein concentration in the solution applied to the membrane was below 0.1 mg/ml, increasing the salt concentration in the dilution solution from 0.1 M to 0.3 M did not reveal any measurable change in spot diameter for a given amount of protein. However, when salt concentration was increased to about 1 M NaCl, protein and SDS precipitated. Thus, salt concentrations above 0.1 M NaCl and less than 1 M NaCl, and particularly between 0.1–0.3 M NaCl, represented saturating salt concentrations.

One purpose of using a saturating salt concentration for protein assay is that once the range of saturating salt concentrations is determined for a particular combination of membrane, detergent, and/or acid, then any salt concentration within this range will be suitable for protein assay of test samples containing varying amounts of salt.

Example 6

Effect of Sample Volume Applied to Protein-Support on Spot Formation

It was observed that when 1 $\mu$l of a BSA solution having a concentration less than 0.1 mg/ml BSA was applied to a protein-support under conditions that work well for more concentrated solutions (e.g., the presence of a spot-sizing combination of detergent, acid and/or salt for a particular membrane used as the protein-support), the protein spot produced generally had a diameter about 1 mm which is difficult to measure. Thus, the effect of increasing the volume applied to the protein-support (in high binding capacity membrane, 300 $\mu$g BSA/cm$^2$ and pore 0.45 $\mu$m) was investigated. It was discovered that applying up to 3–5 $\mu$l of a BSA solution containing less than 0.1 mg/ml produced protein spots having readily measurable diameters which were proportional to the amount of protein applied. Moreover, 4 $\mu$l of a 0.025 mg/ml BSA solution produced spots identical in size to 2 $\mu$l of a twice as concentrated BSA solution, i.e, 0.05 mg/ml. Therefore, within the range of 1 $\mu$l to 5 $\mu$l, the volume of protein solution applied to the protein-support does not affect the linear relationship between the amount of protein applied and the diameter of the spot produced. This allows the assay of protein solutions, preferably those containing less than 0.1 mg/ml protein, to be performed more reliably by applying a larger volume, i.e., up to 3–5 $\mu$l, of the protein solution to the protein-support.

However, when more than 1 $\mu$l of this protein solution (2–5 $\mu$l) was applied to the protein-support membrane impregnated with acid, protein spot formation was adversely affected and protein spots spread widely. It is suspected that when a larger sample volume is applied to the acid treated membrane it washes away the acid on the membrane, thus altering the spot formation property of the protein-support.

Example 7

Effect of Non-ionic Detergents on Protein Spot Formation

The effect on protein spot formation of non-ionic detergents, including Triton X-100, Tween 20, and NP40, at a concentration of 0.1% was also investigated using a 5% TCA impregnated nitrocellulose membrane (binding capacity of 100 $\mu$g BSA/cm$^2$) as the protein-support. The addition of these non-ionic detergents to a protein solution did not show any noticeable change in the diameter of protein spots when compared with spots produced from the same protein solution made in water and without the added non-ionic detergent. However, the addition of non-ionic detergents to this protein solution appeared to produce more uniform spots. Thus, in some protein assays, it may be preferable to prepare the protein solutions using dilution solutions containing both ionic and non-ionic detergents.

The effect of non-ionic detergents may vary with the membrane type as illustrated in a different experiment where a nitrocellulose membrane with a higher protein binding capacity (300 $\mu$g BSA/cm$^2$) was used as the protein-support. In this instance, the membrane was not treated with any acid. A protein solution (2 mg/ml) was serially diluted in dilution solutions containing 1% SDS and from 0.0 M to 0.3 M NaCl (no acid was present in these dilution solutions) and 1 $\mu$l aliquot of the serial dilutions were spotted on the support membrane. It was discovered that as the concentration of salt increased the protein spots decreased in size. A NaCl concentration of about 0.06 to about 0.075 M NaCl represented the spot-sizing concentration for the membrane and detergent concentration used and promoted the formation of protein spots that were proportional to the concentration of total protein in the protein solution applied to the protein-support. Furthermore, at lower protein concentrations (around 0.05 mg/ml) protein spots had 1–2 mm diameters, although they were fainter and diffused in color.

When 0.05% to 1% of a non-ionic detergent was added to the dilution solution, at lower protein concentrations (below 0.2 mg/ml) the protein spots tended to be diffuse and spread widely. Addition of 5% acetic acid (or 0.3 M citric acid) to the dilution solution restrained the spread of the protein solution on the protein-support and produced protein spots having expected diameters which were substantially proportional to protein concentration even at lower protein concentrations. Thus, when using this higher binding capacity membrane as the protein-support, the addition of an acidic agent to the dilution medium and/or the protein-support was found to be necessary for assay of protein solutions containing non-ionic detergents.

Example 8

Lack of Protein-to-Protein Variation

As discussed above, all prior art protein assays show protein-to-protein variation. A number of proteins that have demonstrated large variations in prior art assays (see, e.g., Smith, P. K. et. al. Anal. Biochem. (1985), 150, 76–85) have been tested for protein-to-protein variation using the method of the instant invention. The proteins tested included ribonuclease A, avidin, gelatin, carbonic anhydrase, thyroglobulin, alcohol dehydrogenase, and apoferritin, as well as other proteins. Unlike all previous methods, it was discovered that the protein assay based on the instant invention showed little or no protein-to-protein variation.

Example 9

Effect of Common Reagents in Protein Sample

All prior art protein assays are sensitive to a wide variety of common laboratory agents such as detergents, reducing agents, salts, amines, drugs, antibiotics, dyes, urea, sugars, chelating agents, SDS-PAGE gel loading buffer (containing Tris buffering agents, reducing agents, dyes and glycerol), and so forth. The effect of the presence of the above listed agents in assaying protein solutions with the method of the instant invention was investigated.

A nitrocellulose membrane (300 $\mu$g BSA/cm$^2$ binding capacity and 0.45 $\mu$m pore size) without acid treatment was used as the protein-support. Protein solutions containing various common laboratory agents were serially diluted in a dilution solution containing 1% SDS, 0.037% Triton X-100, 0.3 M citric acid and 0.075 M sodium chloride in such a way that each successive dilution was 2-, 3-, or 5-fold diluted from the previous dilution. An (1 $\mu$l) aliquot of each dilution was applied to the protein-support and protein concentration was determined by averaging the values of more than one protein spot. When selecting protein spots for determination of protein concentration, the protein spots produced from the higher-fold dilutions were preferred over the protein spots of the lower-fold dilutions. In most cases, a 5- to 10-fold dilution in the dilution solution was sufficient to overcome the influence of common laboratory agents present in the protein samples.

In a separate experiment, a dilution solution (1% SDS, 0.037% Triton X-100, 0.3 M citric acid and 0.2 M NaCl) containing a saturating concentration of salt was used for diluting protein solutions containing common laboratory agents; 1 μl of each protein solution was mixed with 4–10 μl of dilution solution; and up to 5 μl aliquot was applied to the protein-support. The protein concentration was determined by measuring the protein spots and comparing to a standard. In most cases, a 2- to 10-fold dilution was sufficient to overcome the influence of common laboratory agents present in the protein solution.

Thus, it was discovered that total protein assay based on the instant invention is substantially not influenced by the presence of common laboratory agents in protein samples because the large dilution of the protein sample in dilution solution greatly reduces or substantially eliminates any influence of such agents.

Example 10

Micro Protein Assay

When protein concentration in a sample drops below 20 μg/ml, applying 1 μl of protein solutions to the protein-support produces spot diameters that are not proportional to protein concentration. i.e., the spots are too small and their diameters can not be measured easily. It was discovered that for assaying dilute protein solutions (having concentrations below 0.5 mg/ml), more reliable results were achieved using a high binding capacity nitrocellulose membrane (not acid treated) as the protein-support and a dilution solution containing a saturating salt concentration (1% SDS, 0.037% Triton X-100, 0.3 M citric acid and 0.2 M NaCl), and applying up to 3–5 μl (or more) protein solution per spot. Under these conditions, the protein assay method of the invention could be used to assay protein solutions containing as little as 0.005 mg/ml BSA, or 5 ng BSA/spot.

More dilute protein solutions were assayed using the limit of detection approach which is illustrated by the following experiment. In this experiment, a protein solution containing 10 μg/ml BSA was serially diluted in dilution solution containing 1% SDS, 5% acetic acid and 0.2 M NaCl such that each successive dilution was 2-, 3-, or 5-fold diluted than the previous dilution. An aliquot (1 μl) from each dilution was applied to a protein-support (nitrocellulose membrane with 300 μg BSA/cm$^2$ binding capacity) and the protein spots were detected using the iodine-starch reaction. It was noticed that protein spots containing less than 0.3 ng were not visible. Thus, the limit of detection of protein spots using the iodine-starch reaction was determined to be 0.3 ng per spot for BSA, and is referred to as the limit of detection factor for BSA.

Determination of concentration for other proteins and other biomolecules may also be performed using the principle of the limitation of detection factor. For example, depending on the limit of detection, a sample solution is serially diluted and applied to the protein-binding medium and the protein-binding medium is treated to detect the spots. The dilution factor or the dilution-fold of the last visible spot is multiplied by the limit of detection factor (e.g., for BSA it is 0.3 ng/spot) for determination of concentration in the sample solution. This method of determination of concentration is suitable not only for protein solutions but other substances, such as nucleic acids, that bind to the protein-binding medium.

Example 11

Assaying Weak Developing Proteins

The method of the present invention may also be used for assay of proteins that would not develop into visible spots or produce faint spots with the iodine-starch reaction. The assay is performed by adding a predetermined amount of standard protein in dilution solution and subtracting the amount of internal standard from the final results. An internal standard may also be used in the assay of various proteins to further reduce any potential protein-to-protein variation.

Example 12

Production of a Protein Gauge

A TCA-impregnated nitrocellulose membrane (binding capacity of 100 μg/cm$^2$) was used as the protein-support. Protein solutions containing 0.01 mg/ml to 5 mg/ml BSA were prepared in Reagent E, a dilution solution containing 1% SDS, 5% acetic acid and 0.075 M NaCl. A 1 μl aliquot from each dilution was applied to the membrane and the spots detected as described above.

Figure 5A:
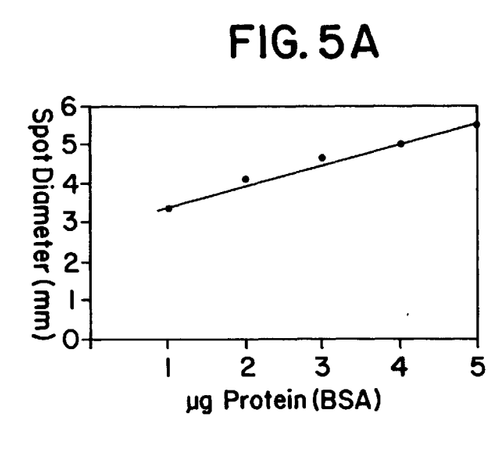
Figure 5B:
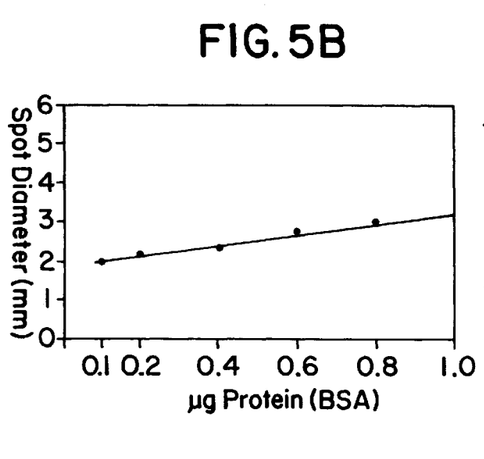
Figure 5C:
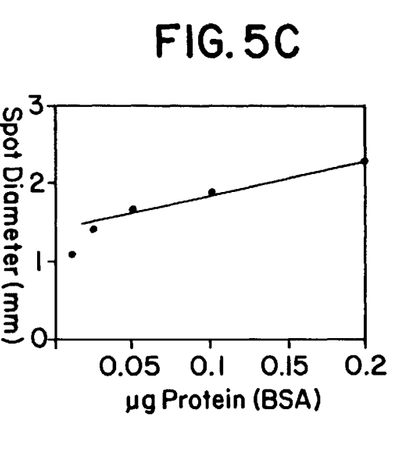

The diameters of the protein spots produced from these solutions of known protein concentration were measured and the data obtained is recorded in Table 1. The data of Table 1 was used to prepare the plot shown in FIG. 5 and the protein gauge shown in FIG. 6, both of which show the linear relationship between protein amount and diameter of protein spots. The protein gauge was transferred to a transparent sheet and used to measure the diameters of protein spots and their corresponding protein amounts. To measure the amount of protein in a protein spot, the gauge was placed on the spot and a position was found where the protein spot fit between the two lines of the protein gauge and the corresponding protein amount was read (see FIG. 3).

TABLE 1

| Scale Scale | Protein Concentration mg/ml | Diameter m.m. |
| --- | --- | --- |
| I | 5 | 5.3 |
|  | 4 | 5.02 |
|  | 3 | 4.66 |
|  | 2 | 4.08 |
|  | 1 | 3.22 |
| II | 0.8 | 2.98 |
|  | 0.6 | 2.74 |
|  | 0.4 | 2.36 |
|  | 0.2 | 2.15 |
| III | 0.1 | 1.9 |
|  | 0.05 | 1.58 |
|  | 0.025 | 1.26 |
|  | 0.0125 | 1.08 |

In an alternative embodiment, a high protein binding capacity nitrocellulose membrane (300 μg BSA/cm$^2$ and pore size of 0.45 μm) was used to prepare a protein gauge. The membrane was used without treating with any acid. Standard protein solutions containing 0.1 mg/ml to 5 mg/ml BSA were prepared in a dilution solution containing 1% SDS, 0.3 M citric acid, 0.037% Triton X-100, and 0.075 M NaCl. A 1 μl aliquot from each dilution was applied to the protein-support.

For assaying more dilute solutions, a second protein gauge was prepared using the same high binding capacity membrane (300 μg BSA/cm$^2$) but using a different dilution solution which contained 1% SDS, 0.037% Triton X-100, 0.3 M citric acid and 0.2 M NaCl, with the NaCl concentration being a "saturating salt concentration". Dilute protein solutions containing 0.0015 mg/ml to 0.1 mg/ml BSA were prepared in this saturating salt concentration dilution solution. An (5 µl) aliquot from each dilution was applied to the protein-support.

Protein spots on both protein-supports were detected with the iodine-starch reaction. Spots produced on both membranes were compact and showed substantially linear relationships. The diameters of spots produced from the more concentrated protein solutions (0.1 mg/ml to 5 mg/ml BSA) ranged from about 1–2 mm to about 5–6 mm. Spots produced from the dilute protein solutions (0.0015 mg/ml to 0.1 mg/ml BSA) ranged from about 0.5 mm to about 2.5 mm. Using the diameters of protein spots, protein gauges were prepared as described above and transferred to a transparent sheet and used for protein assay.

As will be evident to the artisan, various modifications and changes can be made to the above described embodiments and examples without departing from the spirit and scope of the instant invention. For example, a rough estimate of the amount of protein in a sample spot may be obtained by comparing the sample spot to a single standard spot containing a known amount of protein; if the sample spot is smaller than the standard spot, it contains less protein than the standard spot, and if the sample spot is larger than the standard spot, it contains more protein than the standard spot. Therefore reference should be made to the claims in interpreting the breadth of the invention.

I claim:

1. A method for determining the concentration of total protein in a protein solution wherein the total protein refers to all of the protein in a sample, comprising:

applying the protein solution to a protein-support having pores for providing sufficient capillary wicking action so that the protein solution diffuses on the protein-support, in the presence of a detergent and at least one member selected from the group consisting of a salt and an acidic agent in amounts effective to form a substantially uniform protein spot having a size that is proportional to the protein concentration;

measuring the size of the protein spot; and comparing the size of the protein spot containing a total protein concentration with a standard that allows for the determination of the total protein concentration of the protein spot.

2. A method according to claim 1, wherein the protein contacts the protein-support in the presence of each of a detergent, and a salt.

3. A method according to claim 1, wherein the detergent is a mixture of at least one ionic detergent and at least one nonionic detergent.

4. A method according to claim 1, further comprising detecting the protein spot on the protein-support with an iodine-starch reaction.

5. A method according to claim 1, wherein the detergent, and salt, are present at concentrations that produce protein spots showing a substantially linear relationship between the size of protein spots and the protein concentration.

6. A method according to claim 5 wherein said salt concentration is a saturating salt concentration.

7. A method according to claim 1, wherein the protein-support has a pore size larger than 0.2 µm.

8. A method according to claim 7, wherein the pore size is about 0.45 µm.

9. The method according to claim 1, wherein the protein contacts the protein-support in the presence of each of a detergent, a salt and an acidic agent.

10. The method according to claim 9, wherein the detergent, salt, and an acidic agent are present at concentrations that produce protein spots showing a substantially linear relationship between the size of protein spots and the protein concentration.

11. A method according to claim 1, wherein the detergent is selected from the group consisting of ionic and non-ionic detergents.

12. A method according to claim 13, wherein the detergent is an ionic detergent.

13. A method according to claim 12, wherein the detergent is sodium dodecyl sulfate.

14. A method according to claim 1, wherein the protein solution comprises a dilution of a protein sample prepared with a dilution solution.

15. A method according to claim 14, wherein the dilution solution contains a detergent, and at least one member selected from the group consisting of a salt ad an acidic agent.

16. A method according to claim 15, further comprising preparing at least two dilutions of the protein sample by serial dilution and applying each dilution to the protein-support.

17. A method according to claim 1, wherein the protein spot has a substantially circular shape and the size measured, is the diameter of the spot.

18. A method according to claim 17, wherein the standard comprises a display showing a substantially linear relationship between spot diameter and protein amount for at least two substantially circular standard spot containing known, different amounts of a standard protein.

19. A method according to claim 17, wherein the standard comprises one substantially circular standard spot containing a known amount of protein, wherein the standard spot is produced using a combination of a protein-support and chemical agents that produces protein spots having sizes that are linearly proportional to the amount of protein in the spots.

20. A method according to claim 1, wherein the protein-support is a nitrocellulose membrane.

21. A method according to claim 20, wherein the nitrocellulose membrane has a binding capacity for bovine serum albumin of at least 100 µg/cm$^2$.

22. A method according to claim 21, wherein the binding capacity for bovine serum albumin is about 300 µg/cm$^2$.

23. A method according to claim 21, wherein the nitrocellulose -membrane is impregnated with an acidic agent.

24. A method according to claim 23, wherein the acidic agent is selected from the group consisting of trichloroacetic acid, citric acid and phosphoric acid.

25. A kit for determining the concentration of total protein in a protein solution wherein the total protein refers to all of the protein in a sample, comprising:

a protein-support for binding and retaining total protein from a protein solution applied to the protein-support, wherein the protein-support has pores for providing sufficient capillary wicking action so that the protein solution diffuses on the protein-support and is capable of retaining the protein in the form of a substantially circular protein spot having a diameter that is proportional to the concentration of total protein in the solution when the protein contacts the protein-support in the presence of a detergent and at least one member selected from the group consisting of a salt and an acidic agent; and a protein gauge for determining the amount of total protein in the protein spot, wherein the gauge shows a substantially linear relationship between the diameter of the protein spot and the amount of protein in the spot.

26. The kit of claim 25, further comprising:

a dilution solution for preparing the protein solution from a sample; and a reagent solution for visualizing the protein spot on the protein-support medium by an iodine-starch reaction.

27. The kit of claim 26, wherein the dilution solution contains a detergent, and at least one member selected from the group consisting of a salt and an acidic agent.

28. The kit of claim 25 wherein the protein-support is a nitrocellulose membrane having a binding capacity for bovine serum albumin of at least 100 $\mu$g/cm$^2$.

29. The kit of claim 27 wherein the binding capacity for bovine serum albumin is about 300 $\mu$g/cm$^2$.

30. The kit method according to claim 25, wherein the protein-support has a pore size larger than 0.2 $\mu$m.

31. The kit according to claim 30, wherein the pore size of the protein support is about 0.45 $\mu$m.

32. A method for determining the concentration of total protein in a protein solution wherein the total protein refers to all of the protein in a sample, comprising:

applying the protein solution to a protein-support so that the protein solution diffuses into the protein support, said protein-support having pores for providing sufficient capillary wicking action so that the protein solution diffuses on the protein-support, in the presence of a detergent and at least one member selected from the group consisting of a salt and an acidic agent in amounts effective to form a substantially uniform protein spot having a size that is proportional to the protein concentration;

measuring the size of the protein spot; and comparing the size of the protein spot containing a total protein concentration with a standard that allows for the determination of the total protein concentration of the protein spot.

33. The method of claim 32 further comprising retaining the protein solution in a tube having a tip; positioning the tip of the tube over the protein-support so that it touches the protein-support allowing the protein solution to diffuse slowly out of the tube into the protein-support.

* * * * *